United States Patent [19]

Miller

[11] 4,382,231

[45] May 3, 1983

[54] FLUID CONDUCTIVITY SENSOR

[75] Inventor: Francis M. Miller, Snyder, N.Y.

[73] Assignee: Conax Corporation, Buffalo, N.Y.

[21] Appl. No.: 207,340

[22] Filed: Nov. 17, 1980

[51] Int. Cl.$^3$ .............................................. G01N 27/02
[52] U.S. Cl. .................................... 324/439; 340/620;
244/151 B
[58] Field of Search ...................... 340/620; 244/151 B;
73/304 R; 324/439, 446, 449, 450

[56] References Cited

U.S. PATENT DOCUMENTS

| 3,498,131 | 3/1970 | Rickey | 340/620 |
| 3,910,457 | 10/1975 | Sutliff | 222/5 |
| 4,024,440 | 5/1977 | Miller | 361/251 |
| 4,137,527 | 1/1979 | Tennenhouse | 340/620 |
| 4,227,190 | 10/1980 | Kelley et al. | 340/620 |
| 4,253,628 | 3/1981 | Marek | 244/151 B |

Primary Examiner—Michael J. Tokar
Attorney, Agent, or Firm—Christel, Bean & Linihan

[57] ABSTRACT

Apparatus for sensing the electrical conductivity of field including a pair of electrodes and a capacitive type conductivity sensing circuit which in response to the electrodes being exposed to fluid of predetermined minimum conductivity under conditions involving a predetermined minimum rate of change of conductivity applies a gating voltage to the control terminal of a semiconductor device switching it into conduction to define a current flow path through a load. The load can be an ignition capacitor for an electro explosive device which, in turn, can be employed in a release mechanism for uncoupling a parachute canopy from its load upon landing in water. A semiconductor switch defines a discharge path for the ignition capacitor through the electro explosive device. A timing network connected to the ignition capacitor and semiconductor device and including a current regulating device and capacitor causes the semiconductor device to switch into conduction to define the discharge path to detonate the electro explosive device a predetermined time after initiation of charging of the ignition capacitor independent of the rate of charging of the ignition capacitor.

13 Claims, 2 Drawing Figures

FLUID CONDUCTIVITY SENSOR

BACKGROUND OF THE INVENTION

This invention relates to the art of sensing the electrical conductivity of fluid, and more particularly to a new and improved apparatus for sensing and signalling the presence of liquid having a predetermined electrical conductivity.

One area of use of the present invention is detonating an electro explosive device of a release mechanism for uncoupling a parachute canopy from its load upon landing in water, although the principles of the present invention can be variously applied. In the design of such release mechanisms it is obviously important to provide against accidental detonation. Prior art release mechanisms operate when the sensors thereof are immersed in a body of water but many prior art arrangements are susceptible to false detonation when exposed to rain, salt water spray and fog. It would, therefore, be highly desirable to provide fluid conductivity sensing apparatus for providing a signal when exposed to fluid of a predetermined minimum conductivity but which provides no such signal when exposed to rain, salt water spray, fog and similar conditions.

SUMMARY OF THE INVENTION

It is, therefore, a primary object of this invention to provide a new and improved apparatus for sensing the electrical conductivity of fluid.

It is a further object of this invention to provide such apparatus which is operative when exposed to fluid of a predetermined minimum conductivity under conditions involving a predetermined minimum rate of change of conductivity.

It is a more particular object of this invention to provide such apparatus which is operative when exposed to a relatively static body of water but which is insensitive to conditions such as rain, salt water spray and fog.

It is a further object of this invention to provide such apparatus for use with an electro explosive device of a release mechanism for uncoupling a parachute canopy from its load upon landing in water.

The present invention provides apparatus for sensing the electrical conductivity of fluid wherein a conductivity sensing circuit in response to a pair of electrodes being exposed to fluid of predetermined minimum conductivity under conditions of exposure involving a predetermined minimum time rate of change of conductivity between the electrodes applies a voltage to the control terminal of a semiconductor device switching the device into a conducting state to define a current flow path through a load connected to the device. The circuit can be used to detonate an electro explosive device in which case the load includes an ignition capacitor. A semiconductor switch defines a discharge path for the ignition capacitor through the electro explosive device. A timing network connected to the ignition capacitor and to the control terminal of the semiconductor switch controls the time at which the semiconductor device is switched to define the discharge path to detonate the electro explosive device independent of the rate of voltage rise on the ignition capacitor. The electro explosive device can be employed in a release mechanism for uncoupling a parachute canopy from its load upon landing in water.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 1 is an elevational view, partly sectional and partly diagrammatic, showing an illustative canopy release mechanism with which the electrical conductivity sensing apparatus of the present invention can be utilized, the release mechanism being shown in an engaged position and the canopy release body being shown partly in section and partly in phantom outline; and FIG. 2 is a schematic circuit diagram of apparatus for sensing electrical conductivity of fluid according to the present invention.

DETAILED DESCRIPTION OF THE ILLUSTRATED EMBODIMENT

Figure 1:
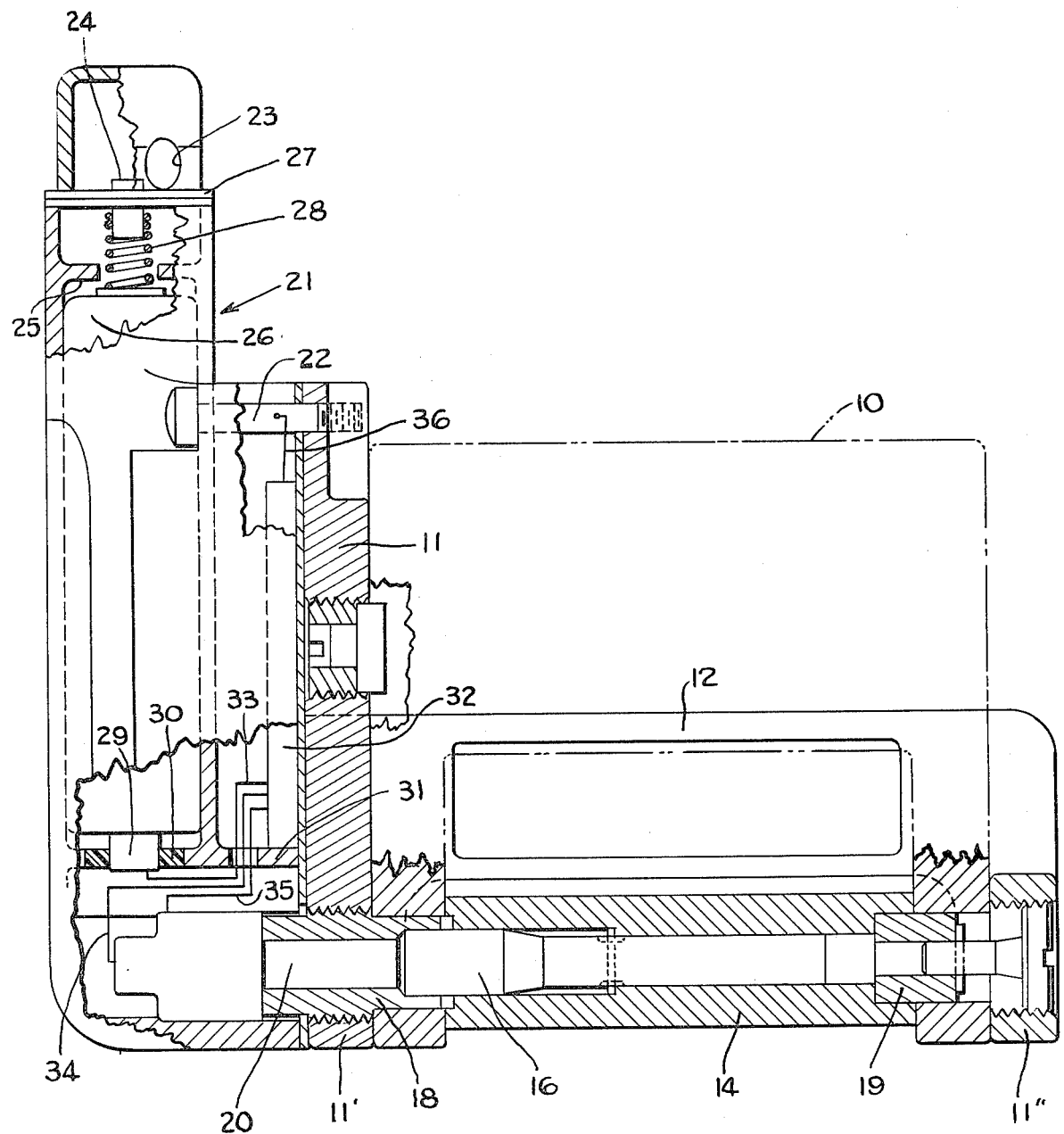

In basic apparatus for sensing electrical conductivity of fluid, when a pair of electrodes is exposed to a conductive fluid a semiconductor device is switched into conduction to define a current path through a load, and the load can include an ignition capacitor for detonating an electro explosive device employed in a release mechanism for uncoupling a parachute canopy from its load upon landing in water. In accordance with the present invention, a conductivity sensing circuit includes capacitive means having a charging rate responsive to the degree of conductivity of a fluid to which sensing electrodes are exposed and to the time rate of change in conductivity of the medium to which the electrodes are exposed whereby when the conductivity and rate of change have predetermined minimum values the rate of voltage rise on the capacitive means is sufficient to apply a gating voltage to the semiconductor device switching it into conduction. In particular, the sensing circuit includes a first capacitor operatively connected to at least one sensing electrode, a series combination of a second capacitor and resistor connected across the first capacitor, the junction of the second capacitor and resistor being connected to the gate terminal of the semiconductor device, and the relative magnitudes of the first and second capacitors and the resistor being selected such that the voltage on the second capacitor cannot increase faster than the voltage on the first capacitor and such that the charging rate of the second capacitor is controlled by the first capacitor.

An ignition capacitor can be connected in series with the semiconductor device for detonating an electro explosive device employed in a release mechanism for uncoupling a parachute canopy from its load upon landing in water. The ignition capacitor is charged when the semiconductor device is switched into conduction by the conductivity sensing circuit, and a semiconductor switch is connected to define a discharge path for the ignition capacitor through the electro explosive device. In accordance with the present invention, a timing network is connected to the ignition capacitor and in controlling relation to the control terminal of the semiconductor switch for causing it to switch to a conducting state to define the discharge path to activate the electro explosive device a predetermined time after initiation of charging of the ignition capacitor independent of the rate of charging of the ignition capacitor. The timing network comprises a voltage controlled normally open switch which when closed applies a gating voltage to the control terminal of the semiconductor switch, a capacitor connected in parallel with the voltage controlled switch for applying a switching voltage thereto, and a current regulating means connected between the capacitor and the ignition capacitor in a manner such that the rate of voltage rises on the capacitor is essentially constant irregardless of the rate of voltage rise on the ignition capacitor.

The apparatus of the present invention, generally speaking, is for sensing the electrical conductivity of a fluid, and one particular use illustrated herein is with a release mechanism for uncoupling a parachute canopy from its load upon landing in water. FIG. 1 shows a portion of a form of canopy release mechanism wherein the locking bar buckle half or body 10 of an illustrative canopy release assembly is shown in outline. A canopy adjuster (not shown) is coupled to the buckle half or canopy release body 10 under control of a conventional double acting manually operable latch mechanism (not shown) in a known manner. An adaptor plate 11 has arms 11', 11" which are joined by a web 12 spanning the canopy release body 10. In the release mechanism shown, a detachable sleeve 14 replaces the existing pin, sleeve and retaining screw (not shown) of the usual canopy assembly. The releasing sleeve 14 has a longitudinal bore in which a release piston 16 is positioned. One end of piston 16 extends beyond sleeve 14 into one end of a cartridge plug 18 which is threaded into the adapter plate 11 and extends into an opening in one arm of the buckle yoke to receive the piston end. The opposite end of sleeve 14 is held in place by a bushing 19 which is seated in the open end of sleeve 14 and extends into an opening in the other arm of the buckle yoke. The piston 16 and bushing 19 are held in the foregoing positions by shear pins to maintain the mechanism in an engaged position.

Plug 18 contains an electro explosive device shown diagrammatically at 20 which is adapted to be fired by operation of the fluid conductivity sensor of the present invention. Typically, the device includes a cartridge at the end adjacent piston 16 and a socket at the opposite end of the device. By way of example, an electro explosive device which will operate satisfactorily in this apparatus is available commercially from Conax Corporation, Buffalo, N.Y. under the designation Part CC12. A housing generally designated 21 is attached to adapter plate 11 by means of mounting screws 22. Water access openings 23 are provided in one end of housing 21 permitting access to a chamber containing a sensing electrode 24. Housing 21 has another interior chamber 25 which contains a voltage source 26 in the form of a battery which is the source of electrical energy for the conductivity sensor. Sensing electrode 24 is connected to one terminal of battery 26, and this can be accomplished by various suitable arrangements. For example, electrode 24 is held in place by a wall 27, at least a portion of which is of electrically insulative material, so that one end of electrode 24 is in the water access chamber closed by wall 27 and electrode 24 is insulated from housing 21. The opposite end of electrode 24 extends beyond wall 27 and is press-fit to one end of a metal spring 28, the opposite end of which contacts one terminal of battery 26 for making electrical connection between the battery terminal and electrode 24. The opposite terminal of battery 26 engages a metal contact 29 which is fitted within an insulator ring 30, the contact-ring combination being secured in an intermediate wall 31 near the lower end of the housing as viewed in FIG. 1. A sensing and firing circuit shown diagrammatically at 32 is located in a portion of housing 21 near adapter plate 11. Circuit 32 is connected by conductor 33 to contact 29 and by conductors 34 and 35 to the two terminals of the electro explosive device 20. A ground or reference point of circuit 32 is connected by a conductor 36 through screw 22 to housing 21. Circuit 32 will be described in detail presently.

Briefly summarizing the operation of the apparatus shown in FIG. 1, when water of predetermined electrical conductivity fills the space between the sensing probe 24 and the body of housing 21, circuit 32 functions to supply after a predetermined time a firing current to electro explosive device 20 to detonate the same. The resulting explosive force acting against the face of piston 16 shears the pin holding piston 16 and drives the piston to the right as viewed in FIG. 1, displacing piston 16 from plug 18 and the yoke arm to a point within sleeve 14, thereby releasing the piston end of sleeve 14 from the buckle frame. After a short distance of axial travel within sleeve 14, the opposite end of piston 16 strikes the end of bushing 19 shearing its pin and driving bushing 19 to the right as viewed in FIG. 1 out of sleeve 14 thereby freeing the bushing end of sleeve 14 from the buckle frame. Sleeve 14 then drops free of the buckle yoke, releasing the load from the canopy. Piston 16 and bushing 19 are wedged or lodged in the release positions thereby precluding any possibility of rebound to interfere with release of sleeve 14 from the buckle frame. For a more detailed description of the construction and operation of the canopy release mechanism shown in FIG. 1, reference may be made to pending U.S. patent application Ser. No. 93,142 filed Nov. 9, 1979 entitled "Canopy Release Mechanism" and assigned to the assignee of the present invention, the disclosure of which is hereby incorporated by reference.

Figure 2:
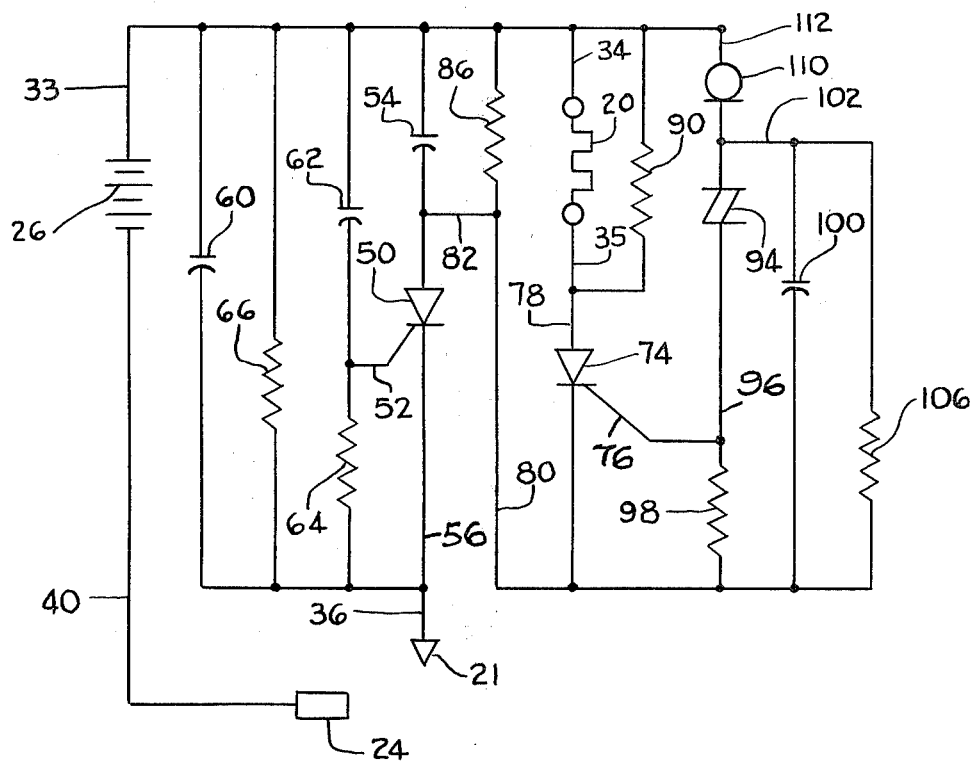

FIG. 2 illustrates in further detail the apparatus for sensing electrical conductivity of a fluid according to the present invention. The apparatus includes a pair of electrodes adapted to be exposed to the fluid. By way of example, when used in a canopy release mechanism as shown in FIG. 1, one of the electrodes is the sensing electrode 24 and the other electrode is the portion of the housing 21 exposed to the water and which is electrically conductive. In the circuit shown in FIG. 2, the housing 21 is identified by a ground or reference symbol. The apparatus further comprises a voltage source having a pair of terminals, one of which is connected to one of the afore-mentioned electrodes. In the circuit shown, the voltage source comprises the battery 26 of FIG. 1 and the negative terminal of battery 26 is connected by a conductor designated 40 to the sensing electrode 24. Conductor 40 can represent spring 28 of the arrangement in FIG. 1.

The apparatus further comprises a three terminal semiconductor device in the form of a silicon controlled rectifier generally designated 50. Controlled rectifier 50 has an anode terminal, a cathode terminal and a control or gate terminal designated 52, and controlled rectifier 50 normally is in a non-conducting state and is adapted to be switched to a conducting state defining a current flow path between the anode and cathode terminals of the rectifier when a voltage of sufficient magnitude is applied to the gate terminal 52. The circuit further comprises a load connected electrically in series with the current flow path of the semiconductor device 50. In the circuit shown the load includes a capacitor 54 and portions of the circuit included to the right of device 50 as shown in FIG. 2 which will be described in detail presently. The combination of the load and the semiconductor device 50 is connected between the other terminal of the voltage source and the other one of the electrodes. In particular, one terminal of capacitor 54 is connected to the anode of controlled rectifier 50 and the other terminal of capacitor 54 is connected to the positive terminal of battery 26. The cathode of controlled rectifier 50 is connected electrically to the portion of housing 21 serving as the other sensing electrode. In particular, the cathode is connected by line 56 to conductor 36 which as shown in FIG. 1 is connected by screw 22 to housing 21.

The apparatus of FIG. 2 further comprises a conductivity sensing circuit connected to the other sensing electrode, i.e. the portion of housing 21 serving as an electrode, to the other voltage source terminal, i.e. the positive terminal of battery 26, and to the gate terminal 52 of the semiconductor device 50. The circuit is responsive to the magnitude or degree of electrical conductivity of fluid to which the electrodes are exposed and to the time rate of change of conductivity in the medium to which the electrodes are exposed, and the circuit applies to the terminal 52 of semiconductor device 50 a voltage of sufficient magnitude to switch device 50 into the conducting state when the electrical conductivity of the fluid is of a predetermined minimum magnitude and when the rate of change in conductivity of the medium to which the electrodes are exposed is of a predetermined minimum magnitude. As a result of the device being switched to a conducting state, a flow of current is allowed through the load connected to device 50. The conductivity sensing circuit includes means having a time varying electrical characteristic wherein the rate of change of the characteristic is proportional to the magnitude or degree of electrical conductivity of the fluid to which the electrodes are exposed and to the rate of change in conductivity of the medium to which the electrodes are exposed. The voltage of sufficient magnitude for switching semiconductor device 50 is applied to terminal 52 of device 50 only when the rate of change of that electrical characteristic reaches a predetermined value.

In particular, the conductivity sensing circuit includes capacitive means having a charging rate responsive to the degree or magnitude of conductivity of the fluid to which the electrodes are exposed and to the time rate of change in conductivity of the medium to which the electrodes are exposed whereby when the degree or magnitude of conductivity is sufficiently large and the rate of change is sufficiently great, the rate of voltage rise on the capacitive means is sufficient to couple the gating or switching voltage to terminal 52 of device 50. In the circuit shown, the sensing circuit comprises a first capacitor 60 connected between the electrodes defined by the portion of housing 21 and the positive terminal of battery 26. The sensing circuit further comprises the series combination of a second capacitor 62 and a resistor 64 connected between the electrode defined by housing portion 21 and the battery positive terminal. The gate terminal 52 of the device 50 is connected to the junction of capacitor 62 and resistor 64. The relative magnitudes of the first capacitor 60, second capacitor 62 and resistor 64 are selected such that the voltage on the second capacitor 62 cannot increase faster than the voltage on the first capacitor 60 and the charging rate of the second capacitor 62 is controlled by the first capacitor 60. The circuit further comprises a bleeder resistor 66 connected across the first capacitor 60.

In operation, when sensing electrode 24 and the associated portion of housing 21 are exposed to fluid having at least some degree of electrical conductivity, there will be some flow of electrical current through the fluid between electrode 24 and the associated portion of housing 21 and through the conductivity sensing portion of the circuit of FIG. 2. In particular, the electron flow is from the negative terminal of battery 26 through conductor 40 to electrode 24 and through the fluid to the housing portion 21 and then through the four parallel circuit paths to the positive terminal of battery 26. Those four paths include capacitor 60, resistor 66, the combination of resistor 64 and capacitor 62, and the path defined by lead 56, the cathode-to-gate path of rectifier 50 and capacitor 62. However, under specified no-fire conditions as determined by the magnitudes of the circuit components, there will be insufficient energy coupled to the gate 52 of controlled rectifier 50 through capacitor 62 to turn the rectifier on and therefore no flow of current through the load, i.e. no charging of capacitor 54. By way of example, when the apparatus is used in a canopy release mechanism, the specified no-fire condition is water having a conductivity of 1000 micro-mhos or less. After capacitors 60 and 62 are charged the current drain on battery 26 is limited by resistor 66. This quiesient condition will continue until the circuit is removed from the no-fire environment and the capacitors are allowed to reset.

In the illustrative use of the apparatus in a canopy release mechanism, the specified all fire condition is water having a conductivity of 10,000 micro-mhos or greater. When the electrodes are exposed to such water the rate of voltage rise on capacitor 60 becomes sufficient to couple the required energy through capacitor 62 to gate 52 of controlled rectifier 50 turning it on and thereby allowing the battery 26 to begin charging the capacitor 54. In addition, the exposure of the electrodes to the electrically conductive fluid under conditions where the rate of change of conductivity is at least a predetermined minimum value. In particular, under conditions where the electrodes have been exposed to atmospheric air and suddenly are exposed to a static body of water having the aforementioned conductivity of 10,000 micor-mhos or greater, both the conductivity of the water and the time rate of change in the conductivity of air to the conductivity of the water are sufficiently great to couple the energy through capacitor 62 to gate rectifier 50 into conduction. In other words, as the parachute and person wearing same descend through the nonconductive air and then suddenly enter a body of water such as the ocean, there is a very rapid rate of change in conductivity sensed by the electrodes and it is a sufficiently rapid rate of rise to cause gating of the rectifier 50 into conduction. However, when the electrodes are exposed to air and thus are exposed to rain, salt water spray or fog, the time rate of change in conductivity from air to the rain, salt water spray or fog is relatively slow and in any event not great enough to couple sufficient energy to gate rectifier 50 into conduction. Such conditions of rain, salt water spray and fog typically are encountered by stationary aircraft on a carrier vessel at sea. In the operation of the sensing circuit to perform the foregoing conductivity and rate of charge determinations, as previously mentioned the voltage or capacitor 62 cannot rise faster than the voltage on capacitor 60 and the charging rate of capacitor 62 is controlled by capacitor 60. The foregoing is believed to result from the selected magnitude of capacitor 60 and the conductivity of the fluid medium between the sensing electrodes relative to the selected magnitudes of capacitor 62 and resistor 64. In addition to the foregoing, capacitor 60 provides static suppression, i.e. prevents inadvertent firing of rectifier 50 by the electrode or housing being exposed to static electricity such as when touched by a person. In the general use of the circuit of the present invention, gating of rectifier 50 to allow current flow through a load, i.e. capacitor 54, is a signal that the fluid has the specified minimum conductivity and that the electrodes have been exposed to at least a certain time rate of change of fluid conductivity, and the signal can be utilized as such. In the illustrative use in a canopy release mechanism, charging of capacitor 54 initiates ignition of the electro explosive device in a manner which will be described. During the charging of capacitor 54 while rectifier 50 conducts, a minute of current will flow through bleeder resistor 86.

The apparatus of FIG. 2 further comprises a two terminal electro explosive device, for example the electro explosive device designated 20 in the illustrative mechanism of FIG. 1. One terminal of device 20 is connected by means of conductor 34 to one terminal of capacitor 54. In the circuit of FIG. 2, capacitor 54 functions as an ignition capacitor for the electro explosive device 70. In particular, capacitor 54 is charged at a rate proportional to the conductivity of the fluid and is charged to a predetermined value of charge while the semiconductor device 50 is in the conducting state. Capacitor 54 then is discharged through the electro explosive device 20 to detonate the same a predetermined thereafter. The circuit of FIG. 2 further comprises semiconductor switching means 74 connected to the other terminal of the electro explosive device 20 and to the other terminal of the ignition capacitor 54. The semiconductor switching means 74 normally is in a nonconducting state and is adapted to be switched to a conducting state when an electrical quantity of predetermined magnitude is applied to a control or gate terminal 76 thereof. When the semiconductor switching means 74 is in the conducting state it defines a discharge path for the ignition capacitor 54 through the electro explosive device 20. In particular, the semiconductor switching means 74 comprises a controlled rectifier, and the anode terminal is connected by line 78 through conductor 35 to the other terminal of electro explosive device 20. The cathode terminal of controlled rectifier 74 is connected by lines 80 and 82 to the other terminal of the ignition capacitor 54. A bleeder resistor 86 is connected between the junction of lines 80, 82 and to the terminal of ignition capacitor 54 connected to electro explosive device 20. A resistor 90 is connected across the electro explosive device 20 to prevent inadvertent firing in a manner which will be described.

The apparatus of FIG. 2 further comprises a timing network connected to the ignition capacitor 54 and connected in controlling relation to the semiconductor switching means 74 for causing the semiconductor switching means to switch to the conducting state to define the discharge state to activate electro explosive device 20 a predetermined time after initiation of charging of the ignition capacitor 54 independent of the rate of charging of the ignition capacitor 54. As previously described, capacitor 54 charges at a rate proportional to the conductivity of the fluid to which the electrodes are exposed, and typically the rate is exponential. The timing network comprises a first branch including a voltage controlled, normally open semiconductor switch 94 which is connected to the control or gate terminal of semiconductor switching means 74 such that when the switch 94 is closed sufficient voltage is applied to the gate terminal 76 to switch device 74 into conduction thereby completing the discharge circuit for ignition capacitor 54 through the electro explosive device 20. In particular, the semiconductor switch 94 is a two terminal device, one terminal of which is connected by line 96 to the gate terminal 76 and to one terminal of a resistor 98, the other terminal of which is connected to line 80.

The timing network further comprises a second branch including a capacitor 100 connected across the first branch so that the voltage on capacitor 100 is applied in controlling relation to the voltage controlled switch 94. In particular, one terminal of capacitor 100 is connected by a line 102 to the other terminal of voltage controlled switch 94. The other terminal of capacitor 100 is connected to the terminal of resistor 98 which is connected to line 80. A bleeder resistor 106 is connected across capacitor 100. The timing network further comprises a current regulating device generally designated 110 connected between capacitor 100 and the ignition capacitor 54 in a manner such that the rate of voltage rise on capacitor 100 is essentially constant regardless of the rate of rise of voltage on the ignition capacitor 54. The current regulating device 110 is a two terminal device, one terminal of which is connected by a line 112 to the terminal of capacitor 54 connected to electro explosive device 20. The other terminal of device 110 is connected by line 102 to the capacitor 100, and that terminal of device 110 also is connected to voltage controlled switch 94.

In operation, as the charge on the ignition capacitor 54 increases over time, the increasing voltage across capacitor 54 is reflected across the timing network including the current regulating device 110, the semiconductor switch 94, capacitor 100 and bleeder resistor 106. Although the rate of voltage rise on the ignition capacitor 54 is exponential and a function of the conductivity of the fluid to which the electrodes are exposed, the current regulating device 110 causes the rate of voltage rise on capacitor 100 to be essentially constant over a widely changing range of applied voltage. When the increasing voltage on capacitor 100 reaches the switching voltage of the semiconductor device 94, the device will turn on discharging capacitor 100 through resistor 98 causing a voltage/current pulse on the control terminal 76 of controlled rectifier 74 causing it to turn on. When controlled rectifier 74 is turned on, the capacitor 54 discharges through the controlled rectifier 74 and the electro explosive device 20 thereby causing explosive ignition of the device 20.

The timing network thus provides a time delay which gives ignition capacitor 54 sufficient time to charge up to a level sufficient to provide the desired energy for firing the electro explosive device, that level preferably being at or near the voltage of battery 26. By way of example, in an illustrative circuit, the time delay from the beginning of charging of ignition capacitor 54 to the detonation of device 20 is 1.5 seconds. The timing network thus insures that electro explosive device 20 is effectively detonated with the proper desired level of energy or voltage and is not detonated until that specified level is reached.

The timing network also prevents accidental detonation of device 20 in response to a component failure or other circuit malfunction. In particular, under such conditions where the circuit would attempt to fire the electro explosive device when such firing is not wanted, the time delay period built into the timing network, i.e. the 1.5 seconds period previously mentioned, will cause controlled rectifier 74 to fire at a time when the voltage on the ignition capacitor 54 is well below the voltage required for firing the electro explosive device so that the device is not fired. For example, assume that the electrodes are exposed to water having an electrical conductivity below that at which it is desired to fire the electro explosive device. There will be a voltage drop between the electrodes and there also will be a voltage drop across ignition capacitor 54 due to the component failure. This voltage drop across capacitor 54, however, will be less, for example eight volts, than the voltage across capacitor 54 under all fire conditions with no component failure. But with the component failure and the passage of time the voltage on capacitor 54 could rise to a level sufficient to detonate the electro explosive device. The provision of the timing network prevents this because it causes controlled rectifier 74 to switch on after a preset time, for example 1.5 seconds, which time is well before the time when the voltage on capacitor 54 would reach a firing level.

By way of example, in an illustrative circuit for use in a canopy release mechanism, battery 26 has a magnitude of 24 volts, capacitor 60 has a magnitude of 78 microfarads at 50 volts d.c., capacitor 62 has a magnitude of 1.0 microfarad at 50 volts d.c., and resistors 64 ad 66 have magnitudes of 1.0 and 100 kilohms, respectively. Capacitor 54 has a magnitude of 220 microfarads at 15 volts d.c., resistors 86 and 106 each have magnitudes of 100 kilohms, resistor 90 has a magnitude of 1 kilohm, resistor 98 has a magnitude of 10 ohms, and capacitor 100 has a magnitude of 33 microfarads at 10 volts d.c. Silicon controlled rectifiers 50 and 74 are type 2N5060, current source 110 is a Motorola 1N5283 0.00022 ampere current regulator, and semiconductor switch 94 is a General Electric 2N4992 silicon bidirectional switch.

It is therefore apparent that the present invention accomplishes its intended objects. While an embodiment of the present invention has been described in detail, this is for the purpose of illustration, not limitation.

I claim:

1. Apparatus for sensing the electrical conductivity of fluid comprising:
   (a) a pair of electrodes adapted to be exposed to said fluid;
   (b) a voltage source having a pair of terminals, one of said terminals being connected to one of said electrodes;
   (c) a three terminal semiconductor device normally in a nonconducting state and adapted to be switched to a conducting state defining a current flow path between two terminals of said device when a voltage of sufficient magnitude is applied to a third terminal of said device;
   (d) a load connected electrically in series with the current flow path of said device;
   (e) said load and said semiconductor device being connected between the other terminal of said voltage source and the other one of said electrodes; and
   (f) a conductivity sensing circuit connected to said other electrode, to said other voltage source terminal and to said third terminal of said semiconductor device, said circuit including means responsive to the electrical conductivity of fluid to which said electrodes are exposed and responsive to the rate of change in electrical conductivity to which said electrodes are exposed for applying to said third terminal of said semiconductor device a voltage of sufficient magnitude to switch said device to said conducting state when the electrical conductivity of said fluid and the rate of change in electrical conductivity each is of a predetermined minimum magnitude thereby allowing a flow of current through said load.

2. Apparatus according to claim 1, wherein said conductivity sensing circuit includes means having a time varying electrical characteristic wherein the rate of change of said characteristic is proportional to the electrical conductivity of the fluid to which said electrodes are exposed and to the rate of change in conductivity, the voltage of sufficient magnitude being applied to said third terminal of said semiconductor device only when the rate of change of said characteristic reaches a predetermined value.

3. Apparatus for sensing the electrical conductivity of fluid comprising:
   (a) a pair of electrodes adapted to be exposed to said fluid;
   (b) a voltage source having a pair of terminals, one of said terminals being connected to one of said electrodes;
   (c) a three terminal semiconductor device normally in a nonconducting state and adapted to be switched to a conducting state defining a current flow path between two terminals of said device when a voltage of sufficient magnitude is applied to a third terminal of said device;
   (d) a load connected electrically in series with the current flow path of said device;
   (e) said load and said semiconductor device being connected between the other terminal of said voltage source and the other one of said electrodes; and
   (f) a conductivity sensing circuit connected to said other electrode, to said other voltage source terminal and to said third terminal of said semiconductor device, said circuit being responsive to the electrical conductivity of fluid to which said electrodes are exposed and to the rate of change in electrical conductivity to which said electrodes are exposed for applying to said third terminal of said semiconductor device a voltage of sufficient magnitude to switch said device to said conducting state when the electrical conductivity of said fluid and the rate of change in electrical conductivity each is of a predetermined minimum magnitude thereby allowing a flow of current through said load, said conductivity sensing circuit including capacitive means having a charging rate responsive to the conductivity of the fluid to which said electrodes are exposed and to the rate of change in conductivity whereby when the degree of conductivity is sufficiently high the rate of voltage rise on said capacitive means is sufficient to couple the voltage of sufficient magnitude to said third terminal of said semiconductor device.

4. Apparatus for sensing the electrical conductivity of fluid comprising:

(a) a pair of electrodes adapted to be exposed to said fluid;

(b) a voltage source having a pair of terminals, one of said terminals being connected to one of said electrodes;

(c) a three terminal semiconductor device normally in a nonconducting state and adapted to be switched to a conducting state defining a current flow path between two terminals of said device when a voltage of sufficient magnitude is applied to a third terminal of said device;

(d) a load connected electrically in series with the current flow path of said device;

(e) said load and said semiconductor device being connected between the other terminal of said voltage source and the other one of said electrodes; and (f) a conductivity sensing circuit connected to said other electrode, to said other voltage source terminal and to said third terminal of said semiconductor device, said circuit being responsive to the electrical conductivity of fluid to which said electrodes are exposed and to the rate of change in electrical conductivity to which said electrodes are exposed for applying to said third terminal of said semiconductor device a voltage of sufficient magnitude to switch said device to said conducting state when the electrical conductivity of said fluid and the rate of change in electrical conductivity each is of a predeterminted minimum magnitude thereby allowing a flow of current through said load, said sensing circuit comprising a series combination of a capacitor and a resistor connected between said other electrode and said other terminal of said voltage source, said third terminal of said semiconductor device being connected to the junction of said coupling capacitor and said resistor.

5. Apparatus for sensing the electrical conductivity of fluid comprising:

(a) a pair of electrodes adapted to be exposed to said fluid;

(b) a voltage source having a pair of terminals, one of said terminals being connected to one of said electrodes;

(c) a three terminal semiconductor device normally in a nonconducting state and adapted to be switched to a conducting state defining a current flow path between two terminals of said device when a voltage of sufficient magnitude is applied to a third terminal of said device;

(d) a load connected electrically in series with the current flow path of said device;

(e) said load and said semiconductor device being connected between the other terminal of said voltage source and the other one of said electrodes;

(f) a conductivity sensing circuit connected to said other electrode, to said other voltage source terminal and to said third terminal of said semiconductor device, said circuit being responsive to the electrical conductivity of fluid to which said electrodes are exposed and to the rate of change in electrical conductivity to which said electrodes are exposed for applying to said third terminal of said semiconductor device a voltage of sufficient magnitude to switch said device to said conducting state when the electrical conductivity of said fluid and the rate of change in electrical conductivity each is of a predetermined minimum magnitude thereby allowing a flow of current through said load;

(g) an electro explosive device; and (h) said load comprising circuit means connected to said electro explosive device for supplying current to said explosive device to detonate said explosive device after said semiconductor device is switched to the conducting state.

6. Apparatus according to claim 4, further including another capacitor connected between said other electrode and said other terminal of said voltage source, the relative magnitudes of said capacitors and said resistor being selected such that the voltage on said first-named capacitor cannot increase faster than the voltage on said other capacitor and the charging rate of said first-named capacitor is controlled by said other capacitor.

7. Apparatus according to claim 6, further including a bleeder resistor connected to said other capacitor in parallel therewith.

8. Apparatus according to claim 5, wherein said circuit means comprises an ignition circuit including an ignition capacitor which is charged to a predetermined value while said semiconductor device is in the conducting state and then is discharged through said electro explosive device to detonate said device.

9. Apparatus according to claim 8, wherein said circuit means further comprises timing circuit means connected to said ignition circuit means and to said electro explosive device for causing detonation of said explosive device a predetermined time after initiation of charging of said ignition capacitor independent of the rate of charging of said ignition capacitor.

10. Apparatus according to claims 5, 8 or 9, wherein said electro explosive device is included in a release mechanism for uncoupling a parachute canopy from its load upon landing in water, said canopy being uncoupled when said electro explosive device is detonated, and said electro explosive device being detonated when said electrodes are exposed to water having a predetermined conductivity under exposure conditions involving a predetermined rate of change in conductivity.

11. In combination with a two terminal electro explosive device, a fluid conductivity responsive circuit for activating said device comprising:

(a) an ignition capacitor having a pair of terminals;

(b) circuit means including at least one electrode adapted to be exposed to fluid for charging said capacitor in response to fluid of a predetermined electrical conductivity being exposed to said electrode, said capacitor being charged at a rate proportional to the degree of conductivity of the fluid;

(c) means for connecting one terminal of said ignition capacitor to one terminal of said electro explosive device;

(d) semiconductor switching means connected to the other terminal of said electro explosive device and to the other terminal of said ignition capacitor, said semiconductor switching means normally being in a nonconducting state and adapted to be switched to a conducting state when an electrical quantity of predetermined magnitude is applied thereto, said semiconductor switching means when in said conducting state defining a discharge path for said ignition capacitor through said electro explosive device; and (e) a timing network connected to said ignition capacitor and connected in controlling relation to said semiconductor switching means for causing said semiconductor means to switch to said conducting state to define said discharge path to activate said electro explosive device a predetermined time after initiation of charging of said ignition capacitor independent of the rate of charging of said ignition capacitor.

12. The combination according to claim 11, wherein said timing network comprises:
   (a) a first branch including a voltage controlled normally open switch and connected to said semiconductor switching means in a manner such that when said switch is closed said electrical quantity of predetermined magnitude is applied to said semiconductor switching means to place said switching means in said conducting state to define said discharge path for said ignition capacitor through said electro explosive device;
   (b) a second branch including capacitive means and connected across said first branch in a manner such that the voltage on said capacitive means is applied in controlling relation to said voltage controlled switch of said first branch; and
   (c) a current regulating means connected between said capacitive means and said ignition capacitor in a manner such that the rate of voltage rise on said capacitive means is essentially constant irregardless of the rate of voltage rise on said ignition capacitor.

13. The combination according to claim 11 or 12, wherein said electro explosive device is included in a release mechanism for uncoupling a parachute canopy from its load upon landing in water, said canopy being uncoupled when said electro explosive device is activated.

* * * * *